United States Patent [19]
Rao

[11] Patent Number: 5,885,801
[45] Date of Patent: Mar. 23, 1999

[54] HIGH THREONINE DERIVATIVES OF α-HORDOTHIONIN

[75] Inventor: Aragula Gururaj Rao, Urbandale, Iowa

[73] Assignee: Pioneer Hi-Bred International, Inc., Des Moines, Iowa

[21] Appl. No.: 824,379

[22] Filed: Mar. 26, 1997

Related U.S. Application Data

[63] Continuation of Ser. No. 459,180, Jun. 2, 1995, abandoned.

[51] Int. Cl.$^6$ .......................... C12N 15/09; C12N 15/29; C12N 15/82; C07K 14/00
[52] U.S. Cl. ............................. 435/69.1; 514/12; 514/2; 530/324; 536/23.6; 435/419; 435/423; 435/424; 435/425; 435/426; 435/252.3
[58] Field of Search ................................ 435/69.1, 170.1, 435/172.3, 419, 423, 424, 425, 426, 252.3; 800/200, 205, 250, DIG. 9, DIG. 52; 935/11, 22; 536/23.6; 514/2, 12; 530/324

[56] References Cited

U.S. PATENT DOCUMENTS 5,703,049  12/1997  Rao .......................................... 514/12

FOREIGN PATENT DOCUMENTS

| | | | |
|---|---|---|---|
| 0 318 341 | 5/1989 | European Pat. Off. | C12N 15/00 |
| 0 502 718 | 9/1992 | European Pat. Off. | C12N 15/00 |
| WO 89/04371 | 5/1989 | WIPO | C12P 21/00 |
| WO 92/14822 | 9/1992 | WIPO | C12N 15/29 |
| WO 93/03160 | 2/1993 | WIPO | C12N 15/82 |
| WO 93/19190 | 9/1993 | WIPO | C12N 15/82 |
| WO 94/10315 | 5/1994 | WIPO | C12N 15/29 |
| WO 94/16078 | 7/1994 | WIPO | C12N 15/29 |
| WO 94/20628 | 9/1994 | WIPO | C12N 15/82 |

OTHER PUBLICATIONS

Florack et al. Synthetic hordothionin genes as tools for bacterial disease resostance breeding. In: Agricultural Biotechnology in Focus in the Netherlands, Dekkers et al, eds. Pudoc, The Netherlands 1990.

Krebber et al. Expression of modified Seed storage proteins in transgenic plants. In:Transgenic Plants. Hiatt, ed. Marcel Dekker, Inc., New York. 1992.

Ponz et al. Cloning and nucleotide sequence of a cDNA encoding the precursor of the barley toxin α–hordothionin. Eur. J. Biochem. vol. 156, pp. 131–135. 1986.

Altenbach S.B. et al., "Manipulation of Methionine—Rich Protein Genes in Plant Seeds" *Trends in Biotechnology*, vol. 8, No. 6, 1990 pp. 156–160.

Altenbach S.B. et al., "Accumulation of a Brazil Nut Albumin Seed of Transgenic Canola Results in Enhanced Level of Seed Protein Methionine", *Plant Molecular Biology*, 18: 235–245, 1992 pp. 235–245.

Anderson J. et al., "A Trasngenic Corn Line with Altered Levels of a High–Methionine Storage Protein", *J. Cell Biochem Suppl.*, vol. 16F, p. 225, 1992, abstract.

Beach, L.R. et al., "Enhancing the nutritional value of Seed Crops", *Current Top. Plant Physiol: Biosynthesis & Molecular Regulation of Amino Acids in Plants*, vol. 7, 1992, pp. 229–238.

Florack, D.E.A et al., "Expression of biologically active hordothionin in tobacco, Effects of pre– and pro–sequences at the amino and carboxyl termini of the hordothionin precursor on mature protein expression and sorting", *Plant Molecular Biology* vol. 24 1994, pp. 83–96.

Garcia–Olmeda, F. et al. "Trypsin/alpha–amylase inhibitors and thionins from cereals: possible role in crop protection", *Journal of Exp. Botany Supplement*, vol. 42, No. 238, May 1991 p. 4 and abstract p. 1.5.

Gordon–Kamm et al. Transformation of Maize Cells and Regeneration of Fertile Transgenic Plants, 1990. *The Plant Cell* 2:603–618.

Karachi H. et al., "Seed Specific Expression of a Bacterial Desensitized Aspartate Kinase Increases the Production of Seed Threonine and Methionine in Transgenic Tobacco", *The Plant Journal*, vol. 3, No. 5, pp. 721–727, 1993.

Karachi H. et al., "Lysine synthesis and catabolism are coordinately regulated during tobacco seed development" PNAS 91, 1994 pp. 2577–2581, p. 2581 left col., last line of right col.

Maddox J. et al. "Cloning of a barley gene alpha–hordothionin, and expression in transgenic tobacco" *J. Cell Biochem. Suppl.* vol. 16F 1992 p. 217 and abstract p. 212.

Ohtari et al. 1991"Normal and lysine–containing zeins are unstable in transgenic tobacco" *Plant Molecular Biol.* 16:117–128.

Ozaki et al. 1980 "Amino Acid Sequence of a Purothionin Homolog from Barley Flour" *J. Biochem* 87.549–555.

Rao A.G. et al., "Validation of the Structure–function properties of alpha–hordothionin and derivatives through protein modeling"–see abstract; *Protein Engineering: Supplement Advances in Gene Technology* Protein Engineering and Beyond. Miami Winter symposium, Jan. 17–22, 1993 vol. 6.

Rao A.G. et al., "Structure–Function Validation of High Lysine Analogs of α–Hordothionin Designed by Protein Modeling", *Protein Engineering*, vol. 7, No. 12, pp. 1485–1493, Dec. 1994.

Reader's Digest "Success with House Plants" *The Reader's Digest Association, Inc.* 1979, pp. 459–461 Huxley et al. (eds).

Rodriguez–Palezuela et al. 1988 "Nucleotide sequence and endosperm–specific expression of the structural gene for the toxin α–hordothionin in barley" *Gene* 70: pp. 271–281.

*Primary Examiner*—Douglas W. Robinson
*Assistant Examiner*—Melissa L. Kimball
*Attorney, Agent, or Firm*—Pioneer Hi-Bred International, Inc.

Derivatives of α-hordothionin made by position-specific substitution with threonine residues provide threonine in pl

HIGH THREONINE DERIVATIVES OF α-HORDOTHIONIN

This is a continuation of application Ser. No. 08/459,180, filed Jun. 2, 1995 now abandoned.

TECHNICAL FIELD

This invention relates to the improvement of feed formulations. Specifically, this invention relates to derivatives of α-hordothionin which provide higher percentages of threonine in plants.

BACKGROUND OF THE INVENTION

Feed formulations are required to provide animals essential nutrients critical to growth. However, crop plants are generally rendered food sources of poor nutritional quality because they contain low proportions of several amino acids which are essential for, but cannot be synthesized by, animals.

For many years researchers have attempted to improve the balance of essential amino acids in the proteins of important crops through breeding programs. As more becomes known about storage proteins and the expression of the genes which encode these proteins, and as transformation systems are developed for a greater variety of plants, molecular approaches for improving the nutritional quality of seed proteins can provide alternatives to the more conventional approaches. Thus, specific amino acid levels can be enhanced in a given crop via biotechnology.

One alternative method is to express a heterologous protein of favorable amino acid composition at levels sufficient to obviate food or feed supplementation. For example, a number of seed proteins rich in sulfur amino acids have been identified. A key to good expression of such proteins involves efficient expression cassettes with seed specific promoters. Not only must the gene-controlling regions direct the synthesis of high levels of mRNA, the mRNA must be translated into stable protein.

Among the essential amino acids needed for animal nutrition, often missing from crop plants, are methionine, threonine and lysine. Attempts to increase the levels of these free amino acids by breeding, mutant selection and/or changing the composition of the storage proteins accumulated in crop plants has met with minimal success. Usually, the expression of the transgenic storage protein was too low. The phaseolin-promoted Brazil nut 2S expression cassette is an example of an effective chimeric seed-specific gene. However, even though Brazil nut protein increases the amount of total methionine and bound methionine, thereby improving nutritional value, there appears to be a threshold limitation as to the total amount of methionine that is accumulated in the seeds. The seeds remain insufficient as sources of methionine.

An alternative to the enhancement of specific amino acid levels by altering the levels of proteins containing the desired amino acid is modification of amino acid biosynthesis. Recombinant DNA and gene transfer technologies have been applied to alter enzyme activity catalyzing key steps in the amino acid biosynthetic pathway. Glassman, U.S. Pat. No. 5,258,300; Galili, et al., European Patent Application No. 485970; (1992); incorporated herein in its entirety by reference. However, modification of the amino acid levels in seeds is not always correlated with changes in the level of proteins that incorporate those amino acids. Burrow, et al., *Mol. Gen. Genet.;* Vol. 241; pp. 431–439; (1993); incorporated herein in its entirety by reference.

Although significant increases in free lysine levels in leaves have been obtained by selection for DHDPS mutants or by expressing the *E. coli* DHDPS in plants, it remains to be shown that these alterations can increase bound target amino acids, which represent some 90% or more of total amino acids. Thus, there is minimal impact on the nutritional value of seeds.

Based on the foregoing, there exists a need for methods of increasing the levels of the essential amino acids, threonine, methionine and lysine in seeds of plants.

It is therefore an object of the present invention to provide methods for genetically modifying plants to increase the levels of the essential amino acid threonine in the plants.

It is a further object of the present invention to provide seeds for food and/or feed with higher levels of the essential amino acid threonine than wild species of the same seeds.

DISCLOSURE OF THE INVENTION

It has now been determined that one class of compounds, the α-hordothionins, can be modified to enhance their content of threonine. α-hordothionin is a 45-amino acid protein which has been well characterized. It can be isolated from seeds of barley (*Hordeum vulgare*). The molecule is stabilized by four disulfide bonds resulting from eight cysteine residues. The amino acid sequence is as provided in SEQUENCE I.D. No.1. In its native form, it is especially rich in arginine and lysine residues, containing 5 residues (10%) of each. However, it contains only 3 residues (7%) of the essential amino acid threonine.

The protein has been synthesized and the three-dimensional structure determined by computer modeling. The modeling of the protein predicts that the ten charged residues (arginine at positions 5,10,17,19 and 30, and lysine at positions 1,23,32,38 and 45) all occur on the surface of the molecule. The side chains of the polar amino acids (asparagine at position 11, glutamine at position 22 and threonine at position 41) also occur on the surface of the molecule. Furthermore, the hydrophobic amino acids (such as the side chains of leucine at positions 8,15 24 and 33 and valine at position 18) are also solvent-accessible.

Three-dimensional modeling of the protein indicates that the arginine residue at position 10 is critical to retention of the appropriate 3-dimensional structure and possible folding through hydrogen bond interactions with the C-terminal residue of the protein. A threonine substitution at that point would disrupt the hydrogen bonding involving arginine at position 10, serine at position 2 and lysine at position 45, leading to destabilization of the structure. The synthetic peptide having this substitution could not be made to fold correctly, which supported this analysis. Conservation of the arginine residue at position 10 provided a protein which folded correctly.

Since threonine is a polar amino acid, the surface polar amino acid residues, asparagine at position 11 and glutamine at position 22, were substituted; and the charged amino acids, lysine at positions 1,23,32 and 38 and arginine at positions 5,17,19, and 30, were substituted with threonine. The resulting compound has the sequence indicated in SEQUENCE I.D. No. 2. The molecule can be synthesized by solid phase peptide synthesis and folds into a stable structure. It has 13 threonine residues (29%).

While SEQUENCE I.D. No. 2 is illustrative of the present invention, it is not intended to be a limitation. Threonine substitutions can also be performed at positions containing charged amino acids. Only arginine at position 10 and lysine at position 45 are critical for maintaining the structure of the protein. One can also substitute at the sites having hydrophobic amino acids. These include positions 8,15,18 and 24. The resulting compound has the sequence indicated in SEQUENCE I.D. NO. 3.

Synthesis of the compounds is performed according to methods of peptide synthesis which are well known in the art and thus constitute no part of this invention. In vitro, the compounds have been synthesized on an applied biosystems model 431a peptide synthesizer using fastmoc™ chemistry involving hbtu (2-(1h-benzotriazol-1-yl)-1,1,3,3-tetramethyluronium hexafluorophosphate, as published by Rao, et al., *Int. J. Pep. Prot. Res.;* Vol. 40; pp. 508–515; (1992); incorporated herein in its entirety by reference. Peptides were cleaved following standard protocols and purified by reverse phase chromatography using standard methods. The amino acid sequence of each peptide was confirmed by automated edman degradation on an applied biosystems 477a protein sequencer/120a pth analyzer. More preferably, however, the compounds of this invention are synthesized in vivo by bacterial or plant cells which have been transformed by insertion of an expression cassette containing a synthetic gene which when transcribed and translated yields the desired compound. Such empty expression cassettes, providing appropriate regulatory sequences for plant or bacterial expression of the desired sequence, are also well-known, and the nucleotide sequence for the synthetic gene, either RNA or DNA, can readily be derived from the amino acid sequence for the protein using standard reference texts. Preferably, such synthetic genes will employ plant-preferred codons to enhance expression of the desired protein.

Industrial Applicability

The following description further exemplifies the compositions of this invention and the methods of making and using them. However, it will be understood that other methods, known by those of ordinary skill in the art to be equivalent, can also be employed.

Plants

The genes which code for these compounds can be inserted into an appropriate expression cassette and introduced into cells of a plant species. Thus, an especially preferred embodiment of this method involves inserting into the genome of the plant a DNA sequence coding for a compound of this invention in proper reading frame, together with transcription initiator and promoter sequences active in the plant. Transcription and translation of the DNA sequence under control of the regulatory sequences causes expression of the protein sequence at levels which provide an elevated amount of the protein in the tissues of the plant.

Preferred plants that are to be transformed according to the methods of this invention are cereal crops, including maize, rye, barley, wheat, sorghum, oats, millet, rice, triticale, sunflower, alfalfa, rapeseed and soybean.

Synthetic DNA sequences can then be prepared which code for the appropriate sequence of amino acids, and this synthetic DNA sequence can be inserted into an appropriate plant expression cassette.

Likewise, numerous plant expression cassettes and vectors are well known in the art. By the term "expression cassette" is meant a complete set of control sequences including initiation, promoter and termination sequences which function in a plant cell when they flank a structural gene in the proper reading frame. Expression cassettes frequently and preferably contain an assortment of restriction sites suitable for cleavage and insertion of any desired structural gene. It is important that the cloned gene have a start codon in the correct reading frame for the structural sequence.

In addition, the plant expression cassette preferably includes a strong constitutive promoter sequence at one end to cause the gene to be transcribed at a high frequency, and a poly-a recognition sequence at the other end for proper processing and transport of the messenger RNA. An example of such a preferred (empty) expression cassette into which the cDNA of the present invention can be inserted is the pPHI414 plasmid developed by Beach, et al., of Pioneer Hi-Bred International, Inc., Johnston, Iowa, as disclosed in U.S. patent application Ser. No. 07/785,648, (1991); incorporated herein in its entirety by reference. Highly preferred plant expression cassettes will be designed to include one or more selectable marker genes, such as kanamycin resistance or herbicide tolerance genes.

By the term "vector" herein is meant a DNA sequence which is able to replicate and express a foreign gene in a host cell. Typically, the vector has one or more endonuclease recognition sites which may be cut in a predictable fashion by use of the appropriate enzyme such vectors are preferably constructed to include additional structural gene sequences imparting antibiotic or herbicide resistance, which then serve as markers to identify and separate transformed cells. Preferred markers/selection agents include kanamycin, chlorosulfuron, phosphonothricin, hygromycin and methotrexate. A cell in which the foreign genetic material in a vector is functionally expressed has been "transformed" by the vector and is referred to as a "transformant."

A particularly preferred vector is a plasmid, by which is meant a circular double-stranded DNA molecule which is not a part of the chromosomes of the cell.

As mentioned above, both genomic and cDNA encoding the gene of interest may be used in this invention. The vector of interest may also be constructed partially from a cDNA clone and partially from a genomic clone. When the gene of interest has been isolated, genetic constructs are made which contain the necessary regulatory sequences to provide for efficient expression of the gene in the host cell. According to this invention, the genetic construct will contain (a) a first genetic sequence coding for the protein or trait of interest and (b) one or more regulatory sequences operably linked on either side of the structural gene of interest. Typically, the regulatory sequences will be selected from the group comprising of promoters and terminators. The regulatory sequences may be from autologous or heterologous sources.

Promoters that may be used in the genetic sequence include NOS, OCS and CaMV promoters.

An efficient plant promoter that may be used is an overproducing plant promoter. Overproducing plant promoters that may be used in this invention include the promoter of the cholorophyll α-βbinding protein and the promoter of the small sub-unit (ss) of the ribulose-1,5-biphosphate carboxylase from soybean. See e.g. Berry-Lowe, et al., *J. Molecular and App. Gen.;* Vol. 1; pp. 483–498; (1982); incorporated herein by reference. These two promoters are known to be light-induced, in eukaryotic plant cells. See e.g., *An Agricultural Perspective,* A. Cashmore, Pelham, New York; pp. 29–38; (1983); G. Coruzzi, et al., *J. Biol. Chem.;* Vol. 258; p. 1399; (1983); and P. Dunsmuir, et al., *J. Molecular and App. Gen.;* Vol. 2; p. 285; (1983); all incorporated herein by reference.

The expression cassette comprising the structural gene for the protein of this invention operably linked to the desired control sequences can be ligated into a suitable cloning vector. In general, plasmid or viral (bacteriophage) vectors containing replication and control sequences derived from species compatible with the host cell are used. The cloning vector will typically carry a replication origin, as well as specific genes that are capable of providing phenotypic selection markers in transformed host cells. Typically, genes conferring resistance to antibiotics or selected herbicides are used. After the genetic material is introduced into the target cells, successfully transformed cells and/or colonies of cells can be isolated by selection on the basis of these markers.

Typically, an intermediate host cell will be used in the practice of this invention to increase the copy number of the cloning vector. With an increased copy number, the vector containing the gene of interest can be isolated in significant quantities for introduction into the desired plant cells. Host cells that can be used in the practice of this invention include prokaryotes, including bacterial hosts such as *E. coli, S. typhimurium,* and *Serratia marcescens.* Eukaryotic hosts such as yeast or filamentous fungi may also be used in this invention. Since these hosts are also microorganisms, it will be essential to ensure that plant promoters which do not cause expression of the protein in bacteria are used in the vector.

The isolated cloning vector will then be introduced into the plant cell using any convenient technique, including electroporation (in protoplasts), retroviruses, bombardment, and microinjection into cells from monocotyledonous or dicotyledonous plants in cell or tissue culture to provide transformed plant cells containing as foreign DNA at least one copy of the DNA sequence of the plant expression cassette. Preferably, the monocotyledonous species will be selected from maize, sorghum, wheat or rice, and the dicotyledonous species will be selected from soybean, alfalfa, rapeseed, sunflower or tomato. Using known techniques, protoplasts can be regenerated and cell or tissue culture can be regenerated to form whole fertile plants which carry and express the gene for a protein according to this invention. Accordingly, a highly preferred embodiment of the present invention is a transformed maize plant, the cells of which contain as foreign DNA at least one copy of the DNA sequence of an expression cassette of this invention.

It will also be appreciated by those of ordinary skill that the plant vectors provided herein can be incorporated into *agrobacterium tumefaciens,* which can then be used to transfer the vector into susceptible plant cells, primarily from dicotyledonous species. Thus, this invention provides a method for increasing threonine levels in *agrobacterium tumefaciens*-susceptible dicotyledonous plants in which the expression cassette is introduced into the cells by infecting the cells with *agrobacterium tumefaciens,* a plasmid of which has been modified to include a plant expression cassette of this invention.

What is claimed is:

1. A protein having the sequence of SEQUENCE I.D. No. 3 wherein the amino acid residues at one or more of positions 1,5,7,8,11,15,17,18,19,22,23,24,30,32,34,38 and 41 are threonine, and the remainder of the residues at those positions are the residues at the corresponding positions in SEQUENCE I.D. No. 1.

2. The protein of claim 1 wherein one or more of the amino acid residues at 1,5,7,11,17,19,22,23,30,32,34,38 and 41 are threonine.

3. The protein of claim 2 wherein at least 5 of the amino acid residues at positions 1,5,7,11,17,19,22,23,30,32,34,38 and 41 are threonine.

4. The protein of claim 3 wherein at least 7 of the amino acid residues at positions 1,5,7,11,17,19,22,23,30,32,34,38 and 41 are threonine.

5. A nucleotide sequence which codes for a protein having the sequence of SEQUENCE I.D. No. 3 wherein the amino acid residues at one or more of positions 1,5,7,8,11,15,17,18,19,22,23,24,30, 32,34,38 and 41 are threonine, and the remainder of the residues at those positions are the residues at the corresponding positions in SEQUENCE I.D. No. 1.

6. An RNA sequence which codes for a protein having the sequence of SEQUENCE I.D. No. 3 wherein the amino acid residues at one or more of positions 1,5,7,8,11,15,17,18,19, 22,23,24,30, 32,34,38 and 41 are threonine, and the remainder of the residues at those positions are the residues at the corresponding positions in SEQUENCE I.D. No. 1.

7. A DNA sequence which codes for a protein having the sequence of SEQUENCE I.D. No. 3 wherein the amino acid residues at one or more of positions 1,5,7,8,11,15,17,18,19, 22,23,24,30,32,34,38 and 41 are threonine, and the remainder of the residues at those positions are the residues at the corresponding positions in SEQUENCE I.D. No. 1.

8. An expression cassette containing the DNA sequence of claim 7 operably linked to plant regulatory sequences which cause the expression of the DNA sequence in plant cells.

9. A bacterial transformation vector comprising an expression cassette according to claim 8, operably linked to bacterial expression regulatory sequences which cause replication of the expression cassette in bacterial cells.

10. Bacterial cells containing as a foreign plasmid at least one copy of a bacterial transformation vector according to claim 9.

11. Transformed plant cells containing at least one copy of the expression cassette according to claim 8.

12. The transformed plant cells of claim 11, wherein the cells are of a monocotyledonous species.

13. The transformed plant cells of claim 12, wherein the cells are selected from the group consisting of maize, sorghum, wheat and rice cells.

14. The transformed cells of claim 11, wherein the cells are of a dicotyledonous species.

15. The transformed cells of claim 14, wherein cells are selected from the group consisting of soybean, alfalfa, rapeseed, sunflower, tobacco and tomato cells.

16. A maize cell or tissue culture comprising cells according to claim 13.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 45 amino acids
        ( B ) TYPE: amino acid
        ( D ) TOPOLOGY: linear ( x i ) SEQUENCE DESCRIPTION: SEQ ID NO:1:

```
Lys  Ser  Cys  Cys  Arg  Ser  Thr  Leu  Gly  Arg  Asn  Cys  Tyr  Asn  Leu  Cys
1                   5                        10                            15

Arg  Val  Arg  Gly  Ala  Gln  Lys  Leu  Cys  Ala  Gly  Val  Cys  Arg  Cys  Lys
               20                       25                       30

Leu  Thr  Ser  Ser  Gly  Lys  Cys  Pro  Thr  Gly  Phe  Pro  Lys
          35                      40                      45
```

( 2 ) INFORMATION FOR SEQ ID NO:2:

( i ) SEQUENCE CHARACTERISTICS:
        ( A ) LENGTH: 45 amino acids
        ( B ) TYPE: amino acid
        ( D ) TOPOLOGY: linear ( x i ) SEQUENCE DESCRIPTION: SEQ ID NO:2:

```
Thr  Ser  Cys  Cys  Thr  Ser  Thr  Leu  Gly  Arg  Thr  Cys  Tyr  Asn  Leu  Cys
1                   5                        10                            15

Thr  Val  Thr  Gly  Ala  Thr  Thr  Leu  Cys  Ala  Gly  Val  Cys  Thr  Cys  Thr
               20                       25                       30

Leu  Thr  Ser  Ser  Gly  Thr  Cys  Pro  Thr  Gly  Phe  Pro  Lys
          35                      40                      45
```

( 2 ) INFORMATION FOR SEQ ID NO:3:

( i ) SEQUENCE CHARACTERISTICS:

-continued (A) LENGTH: 45 amino acids
(B) TYPE: amino acid
(D) TOPOLOGY: linear (xi) SEQUENCE DESCRIPTION: SEQ ID NO:3:

| Thr | Ser | Cys | Cys | Thr | Ser | Thr | Thr | Gly | Lys | Thr | Cys | Tyr | Asn | Thr | Cys |
|---|---|---|---|---|---|---|---|---|---|---|---|---|---|---|---|
| 1 | | | | 5 | | | | | 10 | | | | | 15 | |

| Thr | Thr | Thr | Arg | Ala | Thr | Thr | Thr | Cys | Ala | Gly | Val | Cys | Thr | Cys | Thr |
|---|---|---|---|---|---|---|---|---|---|---|---|---|---|---|---|
| | | | 20 | | | | | 25 | | | | | 30 | | |

| Leu | Thr | Ser | Ser | Gly | Thr | Cys | Pro | Thr | Gly | Phe | Pro | Lys |
|---|---|---|---|---|---|---|---|---|---|---|---|---|
| | | 35 | | | | | 40 | | | | | 45 |